US00PP36428P2

(12) United States Plant Patent
Sluis

(10) Patent No.: US PP36,428 P2
(45) Date of Patent: Feb. 4, 2025

(54) ***YUCCA* PLANT NAMED 'JSCS01'**

(50) Latin Name: *Yucca desmetiana*
Varietal Denomination: JSCS01

(71) Applicant: Janet Sluis, Berkeley, CA (US)

(72) Inventor: Janet Sluis, Berkeley, CA (US)

( * ) Notice: Subject to any disclaimer, the term of this patent is extended or adjusted under 35 U.S.C. 154(b) by 0 days.

(21) Appl. No.: 18/621,215

(22) Filed: Mar. 29, 2024

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373, 263.1
CPC . A01H 5/012; A01H 5/00; A01H 6/12; A01H 5/12
See application file for complete search history.

(56) References Cited

PUBLICATIONS

Greenhouse Management 2024 California Spring Trials Preview: Plant Development Services, Inc., retrieved on Jul. 31, 2024 at https://www.greenhousemag.com/page/plant-development-services-inc-pdsi-california-spring-trials/, 13 pp. (Year: 2024).*

* cited by examiner

*Primary Examiner* — June Hwu
(74) *Attorney, Agent, or Firm* — Cassandra Bright

(57) ABSTRACT

A new and distinct *Yucca* cultivar named 'JSCS01' is disclosed, characterized by green foliage with distinct and uniform white edging on all leaves. This white margin turns pink in cool weather. Plants are slow growing and compact at maturity. Foliage tips are not sharp. The new cultivar is a *Yucca*, suitable for gardens, container cultivation and landscaping.

3 Drawing Sheets

Latin name of the genus and species: *Yucca desmetiana*.
Cultivar denomination: 'JSCS01'.

BACKGROUND OF THE INVENTION

The new cultivar is a product of chance discovery by the inventor in a private garden in Sacramento, California Oct. 26, 2017. This new cultivar, hereinafter referred to as 'JSCS01', was discovered as a naturally occurring, whole plant mutation of the unpatented parent variety *Yucca desmetiana* 'Blue Boy'.

After identifying the new cultivar as a potentially interesting selection, the inventor first organized propagation of 'JSCS01' using tissue culture at a research laboratory in Santa Paula, California. The inventor continued controlled testing and propagation, assessing stability of the unique characteristics of this cultivar. Four generations have been reproduced and has shown that the unique features of this cultivar are stable and reproduced true to type.

SUMMARY OF THE INVENTION

The cultivar 'JSCS01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'JSCS01' These characteristics in combination distinguish 'JSCS01' as a new and distinct *Yucca* cultivar:

1. Uniform white edging on all leaves.
2. Edging turns pink in cool weather (winter color).

3. Center leaf color is green; most *Yucca desmetiana* foliage is grey-blue.
4. Plants are slow growing and compact at maturity.
5. Foliage tips are not sharp.

COMPARISON TO PARENT CULTIVAR

'JSCS01' is similar to the parent *Yucca desmetiana* 'Blue Boy' in most horticultural characteristics, however, plants of the new cultivar 'JSCS01' differ in the following:

1. The new cultivar has green foliage with distinct, uniform white margins; this comparator has entirely grey-green foliage which develops a burgundy tone in cold weather.
2. The new cultivar grows more slowly than this comparator, which grows rapidly to 6 feet in height.

COMMERCIAL COMPARISON

'JSCS01' can be compared to the commercial cultivar *Yucca aloifolia* 'Magenta Magic', unpatented. Plants of the new cultivar 'JSCS01' are similar to plants of 'Magenta Magic' in most horticultural characteristics, however, plants of the new cultivar 'JSCS01' differ in the following;

1. The new cultivar has a definite white foliar margin; this comparator has solid green foliage.

BRIEF DESCRIPTION OF THE PHOTOGRAPHS

The accompanying photograph in FIG. 1 illustrates in full color a 6-year old plant grown outdoors in Sacramento, California photographed during late Winter months. This plant shows the distinctive pink foliar color found in colder temperatures.

Figure 1:
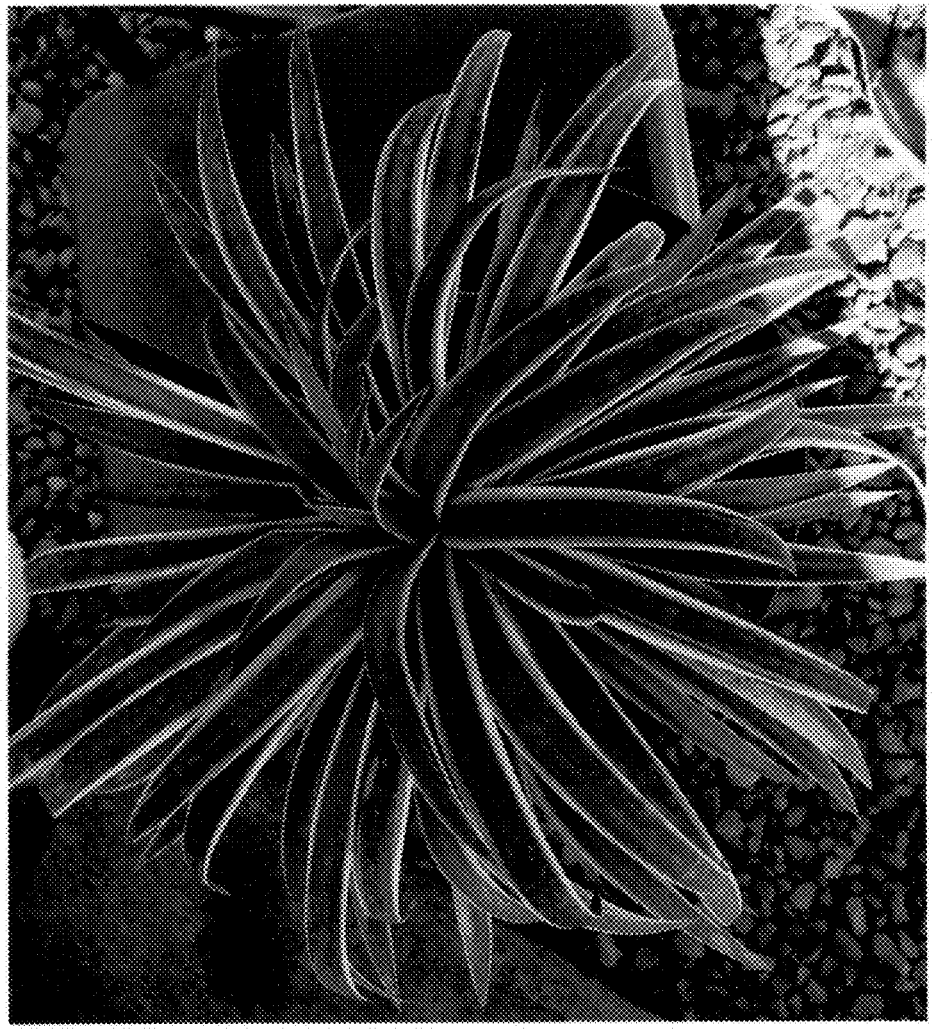
Figure 2:
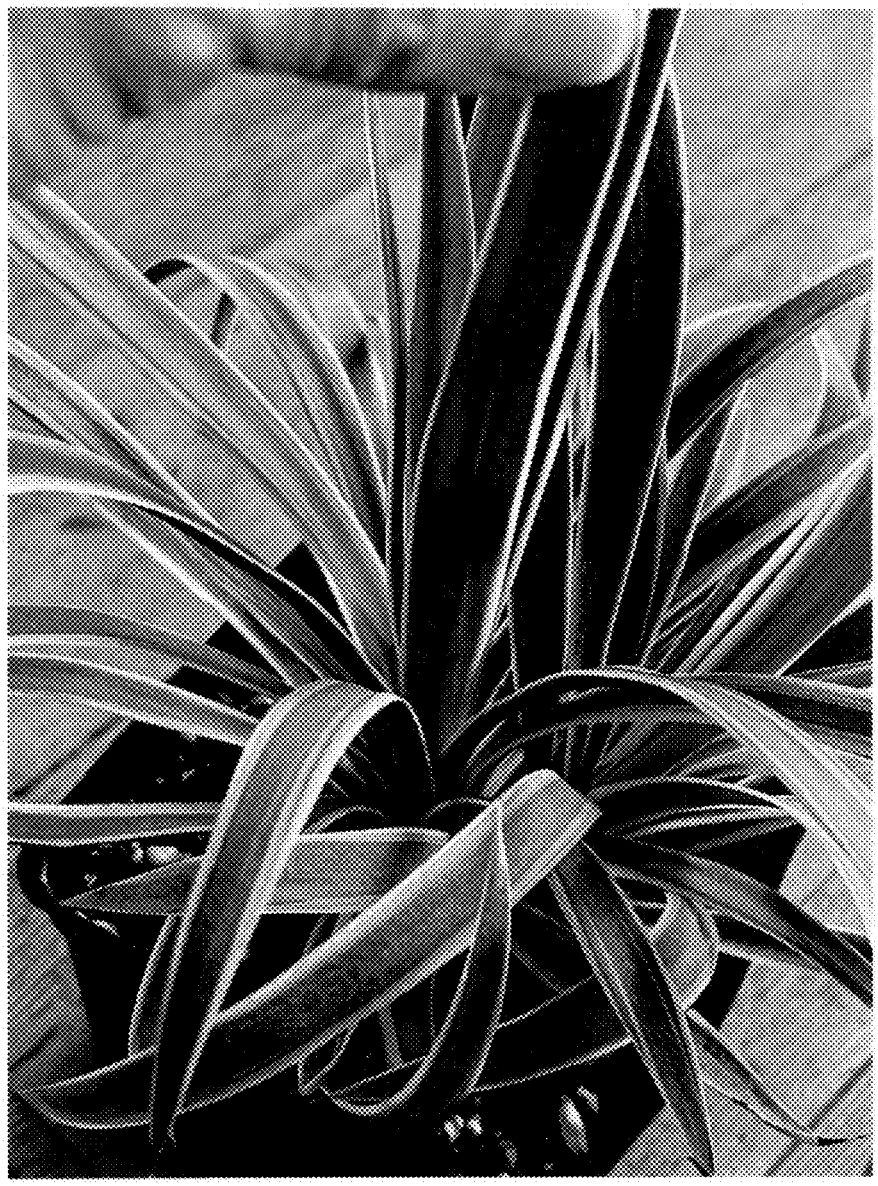
FIG. 2 is 1-year old plant of 'JSCS01' grown outdoors in Santa Paula, CA where temperatures did not reach below 6° C. Only faint pink coloration can be seen.
Figure 3:
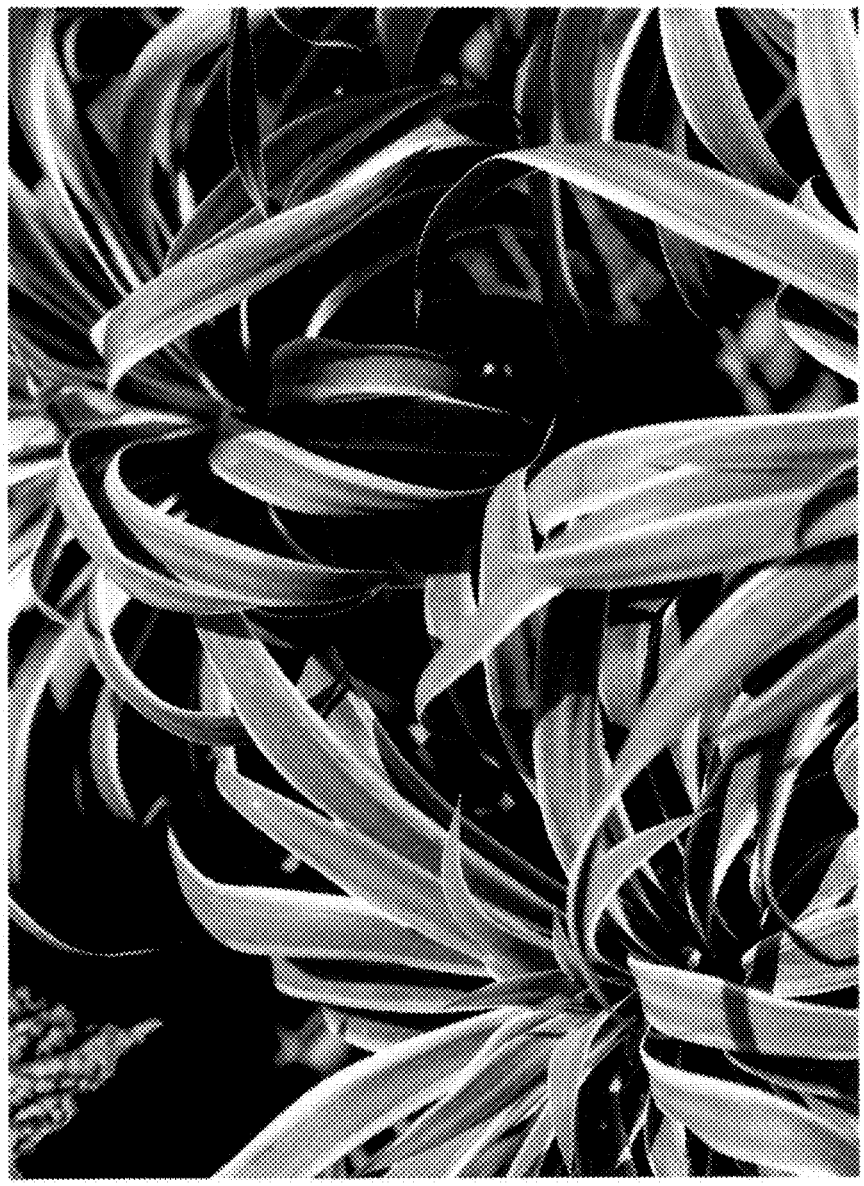
FIG. 3 is a 1-year-old plant in a 9.5 inch pot grown in a greenhouse with warm conditions. No pink is visible on the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'JSCS01' plants grown outdoors in a greenhouse in Santa Paula, California. Plants are approximately 1 year old. Measurements and numerical values represent averages of typical plant types.

Botanical classification: *Yucca desmetiana* 'JSCS01'.

ROOTS

Root description: Fine and fibrous, colored near Yellow-White RHS 158A.

PLANT

Growth habit: Upright rosette.
Height: Approximately 38 cm to top of highest leaf.
Plant spread: Approximately 33 cm in a 9.5 inch pot.
Growth rate: Slow.
Stem: About 1.5 cm in dimeter.
Number of leaves per plant: Approximately 30 to 40 on a 1-year old plant.
Age of plant described: Approximately 1 year.

FOLIAGE

Leaf:

*Arrangement*.—Spiral.
*Average length*.—Average 22 cm.
*Average width*.—Average 1.75 cm.
*Shape of blade*.—Linear.
*Aspect*.—Moderately arched.
*Apex*.—Acuminate with soft tip.
*Base*.—Truncate.
*Margin*.—Entire
*Texture of top surface*.—Smooth.
*Texture of bottom surface*.—Smooth.
*Appearance*.—Matte to very slightly glaucous all surfaces.
*Color*.—Summer foliage upper side: Near RHS Green 137C, margin near White 155D. Marginal color 5 to 15 mm wide, solid along margin. Some white streaking next to margin. Summer foliage under side: Near RHS Green 137C, margin near White 155D. Marginal color 5 to 15 mm wide, solid along margin. Some white streaking next to margin. Winter foliage upper side: Near RHS Green 137C, margin near White 155D. Marginal color 5 to 15 mm wide, solid along margin. Some white streaking next to margin. Margin flushed Red 50D and 52D. In temperatures near freezing an overlay of Greyed-Purple N186C covers the entire leaf blade. Winter foliage under side: Near RHS Green 137C, margin near White 155D. Marginal color 5 to 15 mm wide, solid along margin. Some white streaking next to margin. Margin flushed Red 50D and 52D. In temperatures near freezing an overlay of Greyed-Purple N186C covers the entire leaf blade.

Venation:

*Type*.—Parallel.
*Venation coloration upper side*.—Indistinguishable from leaf blade.
*Venation coloration under side*.—Indistinguishable from leaf blade.

FLOWER

Not observed to date.

OTHER CHARACTERISTICS

Disease and pest resistance: Neither resistance nor susceptibility to normal diseases and pests of *Yucca* observed. While *Yucca* is not typically susceptible to diseases and pests, potential insect problems include spider mites (*Tetranychus urticae*) mealybugs (*Planococcus citri*) and scale (*Asterolecanium grandiculum*). The most common disease is leafspot (*Coniothryium* or *Cercospora*).

Temperature tolerance: −12° C. to 43° C.

Fruit/seed production: Not observed to date.

What is claimed is:

1. A new and distinct cultivar of *Yucca* plant named 'JSCS01' as herein illustrated and described.

* * * * *